United States Patent
Ji et al.

(10) Patent No.: US 11,753,389 B2
(45) Date of Patent: Sep. 12, 2023

(54) METHOD FOR PREPARING DIHYDROQUERCETIN

(71) Applicant: HEFEI LIFEON PHARMACEUTICAL CO., LTD., Anhui (CN)

(72) Inventors: Junqiu Ji, Anhui (CN); Xiaochang Li, Anhui (CN); Bing Li, Anhui (CN); Qiao Li, Anhui (CN); Qing Miao, Anhui (CN); Limei Liu, Anhui (CN); Jinping Liu, Anhui (CN)

(73) Assignee: HEFEI LIFEON PHARMACEUTICAL CO., LTD., Anhui (CN)

( * ) Notice: Subject to any disclaimer, the term of this patent is extended or adjusted under 35 U.S.C. 154(b) by 0 days.

(21) Appl. No.: 18/008,044

(22) PCT Filed: May 7, 2022

(86) PCT No.: PCT/CN2022/091499
§ 371 (c)(1),
(2) Date: Dec. 2, 2022

(87) PCT Pub. No.: WO2022/237689
PCT Pub. Date: Nov. 17, 2022

(65) Prior Publication Data
US 2023/0192639 A1    Jun. 22, 2023

(30) Foreign Application Priority Data

May 10, 2021    (CN) .......................... 202110519620.6

(51) Int. Cl.
*C07D 311/32*    (2006.01)
*C07D 311/40*    (2006.01)

(52) U.S. Cl.
CPC .......... *C07D 311/32* (2013.01); *C07D 311/40* (2013.01)

(58) Field of Classification Search
CPC .................................................. C07D 311/32
See application file for complete search history.

(56) References Cited

U.S. PATENT DOCUMENTS 2,744,920 A * 5/1956 Kurth .................. C07D 311/30
554/7
2016/0362401 A1    12/2016 Venkateswara et al.

FOREIGN PATENT DOCUMENTS

| CN | 101863869 A | 10/2010 |
| CN | 101993429 A | 3/2011 |
| CN | 103044379 A | 4/2013 |
| CN | 103570663 A | 2/2014 |
| CN | 104024229 A | 9/2014 |
| CN | 104024429 A | 9/2014 |
| CN | 104387357 A | 3/2015 |
| CN | 105283442 A | 1/2016 |
| CN | 105348063 A | 2/2016 |
| CN | 106103419 A | 11/2016 |
| CN | 107880081 A | 4/2018 |
| CN | 110467592 A | 11/2019 |
| CN | 112375043 A | 2/2021 |
| CN | 113185485 A | 7/2021 |
| CN | 113214210 A | 8/2021 |
| EP | 2143435 A | 1/2010 |
| EP | 2850069 A1 | 3/2015 |
| WO | WO 2013/172693 A1 | 11/2013 |

OTHER PUBLICATIONS

International Search Report and Written Opinion for International App. No. PCT/CN2022/091499 dated Jul. 27, 2022.
Yu et al., Review on the Properties of Thiourea Dioxide and Reduction of Organic Compounds with It. Fine Chem. Intermediates. Jun. 30, 2014;44(3). 5 pages.

* cited by examiner

*Primary Examiner* — Valerie Rodriguez-Garcia
(74) *Attorney, Agent, or Firm* — Wolf, Greenfield & Sacks, P.C.

(57) ABSTRACT

The present disclosure provides a preparation method of dihydroquercetin, belonging to the field of synthesis of drugs. The method includes steps of: adjusting reaction solvent water to be alkaline with an alkalizing reagent, to obtain an alkaline aqueous solution; dissolving quercetin dihydrate in the alkaline aqueous solution, and adding a sulfite binary combined reducing agent to carry out reduction reaction, to obtain an endpoint reduction reaction solution; diluting the endpoint reduction reaction solution with water, and then acidizing, aging, and filtering the resultant to obtain a filtrate and a filter cake; subjecting the filtrate to extraction, washing, drying, and vacuum concentration to obtain a concentrated crude product; and repeatedly crystallizing the concentrated crude product to obtain dihydroquercetin. The preparation method of the present disclosure has readily available raw materials, a simple process, and low production costs, and is particularly suitable for industrial production.

20 Claims, 9 Drawing Sheets

Chromatographic peak result

| | Retention time | Area | %Area | Peak height |
|---|---|---|---|---|
| 1 | 7.258 | 2728 | 0.02 | 208 |
| 2 | 14.564 | 3777 | 0.03 | 278 |
| 3 | 16.599 | 70358 | 0.64 | 4289 |
| 4 | 17.692 | 2393 | 0.02 | 173 |
| 5 | 24.296 | 84031 | 0.76 | 4434 |
| 6 | 29.390 | 54875 | 0.50 | 3193 |
| 7 | 36.067 | 7822 | 0.07 | 435 |
| 8 | 37.454 | 6186 | 0.06 | 364 |
| 9 | 39.985 | 5663 | 0.05 | 322 |
| 10 | 41.345 | 8865081 | 80.58 | 404585 |
| 11 | 42.981 | 639407 | 5.81 | 30457 |
| 12 | 43.760 | 753053 | 6.84 | 35276 |
| 13 | 47.410 | 4485 | 0.04 | 230 |
| 14 | 48.359 | 126751 | 1.15 | 5656 |
| 15 | 49.472 | 291767 | 2.65 | 12099 |
| 16 | 51.038 | 37590 | 0.34 | 1575 |
| 17 | 51.948 | 9860 | 0.09 | 485 |
| 18 | 58.876 | 6522 | 0.06 | 348 |
| 19 | 62.202 | 29245 | 0.27 | 1247 |

Report user: Bing Li (13383)
Report method: Dihydroquercetin report
Report method ID: 20032003
Page: 1 (total 1)

Project name: HYB-1901\Laboratory test detection\synthesis chamber
Printing date:
Mar. 5, 2021
17:18:25 PRC

FIG. 1B

Chromatographic peak result

|   | Retention time | Area | %Area | Peak height |
|---|---|---|---|---|
| 1 | 41.218 | 8121646 | 95.93 | 345467 |
| 2 | 43.620 | 63650 | 0.75 | 2754 |
| 3 | 48.212 | 62473 | 0.74 | 2556 |
| 4 | 49.173 | 123544 | 1.46 | 5159 |
| 5 | 62.010 | 94957 | 1.12 | 4292 |

Report user: Bing Li (13383)  
Report method: Dihydroquercetin report  
Report method ID: 20032003  
Page: 1 (total 1)

Project name: HYB-1901\Laboratory test detection\synthesis chamber  
Printing date:  
Mar. 5, 2021  
17:18:13 PRC

FIG. 2B

Chromatographic peak result

|   | Retention time | Area | % Area | Peak height |
|---|---|---|---|---|
| 1 | 26.010 | 2325 | 0.00 | 177 |
| 2 | 41.208 | 84547663 | 99.64 | 4033990 |
| 3 | 43.683 | 258599 | 0.30 | 10661 |
| 4 | 47.925 | 865 | 0.00 | 186 |
| 5 | 48.182 | 16807 | 0.02 | 607 |
| 6 | 62.066 | 23830 | 0.03 | 1026 |

Report user: Bing Li (13383)  
Report method: Dihydroquercetin report  
Report method ID: 20032003  
Page: 1 (total 1)

Project name: HYB-1901\Laboratory test detection\synthesis chamber  
Printing date:  
Mar. 5, 2021  
17:18:02 PRC

FIG. 3B

Chromatographic peak result

| | Retention time | Area | %Area | Peak height |
|---|---|---|---|---|
| 1 | 7.275 | 36366 | 0.32 | 2272 |
| 2 | 13.600 | 9262 | 0.08 | 516 |
| 3 | 14.607 | 41947 | 0.37 | 2751 |
| 4 | 16.649 | 745381 | 6.50 | 41790 |
| 5 | 17.706 | 31719 | 0.28 | 1527 |
| 6 | 24.325 | 888749 | 7.75 | 41682 |
| 7 | 26.207 | 7242 | 0.06 | 339 |
| 8 | 29.377 | 535299 | 4.67 | 26827 |
| 9 | 31.292 | 2606 | 0.02 | 168 |
| 10 | 32.838 | 12869 | 0.11 | 516 |
| 11 | 36.012 | 119349 | 1.04 | 4815 |
| 12 | 37.400 | 75849 | 0.66 | 3615 |
| 13 | 39.940 | 77770 | 0.68 | 3293 |
| 14 | 41.304 | 5275803 | 46.03 | 211827 |
| 15 | 42.913 | 1410302 | 12.31 | 58394 |
| 16 | 43.699 | 849437 | 7.41 | 33695 |
| 17 | 44.817 | 6488 | 0.06 | 320 |
| 18 | 45.568 | 2943 | 0.03 | 188 |
| 19 | 46.208 | 11980 | 0.10 | 537 |
| 20 | 48.272 | 361400 | 3.15 | 14176 |
| 21 | 49.279 | 534766 | 4.67 | 20021 |
| 22 | 50.889 | 164765 | 1.44 | 6350 |
| 23 | 51.819 | 36254 | 0.32 | 1419 |
| 24 | 58.160 | 18063 | 0.16 | 819 |
| 25 | 62.060 | 173157 | 1.51 | 7450 |
| 26 | 63.005 | 31268 | 0.27 | 1471 |

Report user: Bing Li (13383)
Report method: Dihydroquercetin report
Report method ID: 20032003
Page: 1 (total 2)

Project name: HYB-1901\Laboratory test detection\synthesis chamber
Printing date:
Mar. 5, 2021
17:17:46 PRC

FIG. 4B

METHOD FOR PREPARING DIHYDROQUERCETIN

CROSS-REFERENCE TO RELATED APPLICATIONS

The present disclosure is a National Stage filing under 35 U.S.C. 371 of International PCT Application No. PCT/CN2022/091499, filed May 7, 2022, which claims the priority to the Chinese patent application with the filing No. "CN 202110519620.6" filed with the Chinese Patent Office on May 10, 2021 and entitled "Preparation Method of Dihydroquercetin", the contents of which are incorporated herein by reference in entirety.

TECHNICAL FIELD

The present disclosure relates to the field of synthesis of drugs, and in particular, to a preparation method of dihydroquercetin.

BACKGROUND ART

Dihydroquercetin, having a chemical name of 3,3',4',5,7-pentahydroxy-flavanonol, is also called as taxifolin, and has a structural formula as follows:

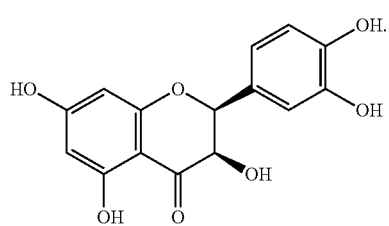

Formula (I)

Compared with quercetin, dihydroquercetin has better dissolving behavior in ethanol and water, and thus has broader and more practical biological activity than quercetin, such as: oxidation resistance, or affecting fat metabolism by regulating enzyme activity, or inhibiting growth of malignant lymphocytes and leukemia cells, or functioning to inhibit bacteria (Staphylococcus aureus, Escherichia coli, Shigella dysenteriae, and Typhoid bacillus, etc.), and also inhibiting viral enzymes. Therefore, the dihydroquercetin has a good promotion and application prospect in fields such as health care products, functional foods, medicines, cosmetics, and industry and agriculture.

Up to now, preparation methods of dihydroquercetin are mainly a phytochemistry method and a chemical synthetic method. The dihydroquercetin has a low content in plants, separation and purification processes after extraction are complex, and the phytochemistry method is destructive to plant resources (such as roots of Pseudotsuga menziesii) under condition of large-scale production. The chemical synthetic method can be divided into a full-synthetic method and a semi-synthetic method. Although the former has readily available raw materials and is easy to achieve large-scale production, the synthesis steps are relatively long, and there are problems such as toxicity of raw materials, reagents, and solvents and different degrees of "three-waste" contamination, therefore, the industrial application prospect is not promising. On the other hand, unless asymmetric synthetic method is employed, the full-synthetic method can hardly render a target product with trans configuration consistent with natural dihydroquercetin.

SUMMARY

The present disclosure provides a preparation method of dihydroquercetin, including the following steps:
adjusting reaction solvent water to be alkaline with an alkalizing reagent, to obtain an alkaline aqueous solution;
dissolving quercetin dihydrate in the alkaline aqueous solution, and adding a sulfite binary combined reducing agent to carry out reduction reaction, to obtain an endpoint reduction reaction solution;
diluting the endpoint reduction reaction solution with water, and then acidizing, aging, and filtering the resultant to obtain a filtrate and a filter cake;
subjecting the filtrate to extraction, washing, drying, and vacuum concentration to obtain a concentrated crude product; and
repeatedly crystallizing (recrystallizing) the concentrated crude product to obtain dihydroquercetin.

In some embodiments, a mass ratio of the quercetin dihydrate to the reaction solvent water is 1:80-200.

In some embodiments, the mass ratio of the quercetin dihydrate to the reaction solvent water is 1:100-180.

In some embodiments, the mass ratio of the quercetin dihydrate to the reaction solvent water is 1:120-160.

In some embodiments, a molar ratio of the quercetin dihydrate to the alkalizing reagent is 1:3.5-5.5.

In some embodiments, a molar ratio of the quercetin dihydrate to the alkalizing reagent is 1:4.0-5.0.

In some embodiments, a molar ratio of the quercetin dihydrate to the sulfite binary combined reducing agent is 1:3-8.

In some embodiments, the molar ratio of the quercetin dihydrate to the sulfite binary combined reducing agent is 1:4.5-7.5.

In some embodiments, the molar ratio of the quercetin dihydrate to the sulfite binary combined reducing agent is 1:5.0-6.0.

In some embodiments, the sulfite binary combined reducing agent includes a binary combination of sodium hydrosulfite and sodium pyrosulfite, or a binary combination of sodium hydrosulfite and sodium bisulfite.

In some embodiments, the sulfite binary combined reducing agent includes a binary combination of sodium hydrosulfite and sodium pyrosulfite.

In some embodiments, a molar ratio of the sodium hydrosulfite to the sodium pyrosulfite is 1:0.15-0.45. In some typical embodiments, the molar ratio of the sodium hydrosulfite to the sodium pyrosulfite is 1:0.2-0.40. In some more typical embodiments, the molar ratio of the sodium hydrosulfite to the sodium pyrosulfite is 1:0.25-0.35.

In some embodiments, a reaction temperature of the reduction reaction is 60-120° C., and reaction time is 55-115 min.

In some embodiments, the reaction temperature of the reduction reaction is 80-100° C., and the reaction time is 70-100 min.

In some embodiments, a mass ratio of the reaction solvent water to water used for dilution after the reduction reaction is 1:0.1-0.6. In some embodiments, the mass ratio of the reaction solvent water to the water used for dilution after the reduction reaction is 1:0.2-0.5.

In some embodiments, the acidizing refers to acidizing, with a dilute acid, the endpoint reduction reaction solution diluted with water.

In some embodiments, a pH value of an acidification endpoint is 0.5-4.0. In some typical embodiments, the pH value of the acidification endpoint is 1.5-3.0.

In some embodiments, a solution temperature of the acidizing process is 0-35° C. In some typical embodiments, the solution temperature of the acidizing process is 15-25° C.; and In some embodiments, the dilute acid includes dilute hydrochloric acid, dilute sulfuric acid, or dilute acetic acid. In some typical embodiments, the dilute acid is dilute sulfuric acid.

In some embodiments, mass concentration of the dilute sulfuric acid is 5%-15%. In some typical embodiments, the mass concentration of the dilute sulfuric acid is 8%-12%.

In some embodiments, the filter cake is recycled after being washed and purified with hot water.

In some embodiments, the hot water is water of 50° C.-100° C. In some typical embodiments, the hot water is water of 65° C.-85° C.

In some embodiments, the washing lasts for 10-30 min. In some typical embodiments, the washing lasts for 15-25 min.

In some embodiments, an extraction solvent used in the extraction is a hydrophobic organic solvent.

In some embodiments, the hydrophobic organic solvent includes at least one of an aliphatic ether, an alicyclic ether, an aliphatic ester, and a hydrophobic aliphatic ketone.

In some embodiments, the hydrophobic organic solvent includes at least one of isopropyl ether, tert-butyl ether, ethyl acetate, isopropyl acetate, and methyl isobutyl ketone.

In some embodiments, a process of the repeatedly crystallizing includes: subjecting the concentrated crude product to primary crystallization to obtain a primary crystallization substance (primary crystallization product); and crystallizing the primary crystallization substance secondarily to obtain a secondary crystallization substance (secondary crystallization product).

In some embodiments, the solvent used for repeated crystallization (recrystallization) includes a mixed solvent of lower aliphatic alcohol and water. In some typical embodiments, the lower aliphatic alcohol includes at least one of methanol, ethanol, and isopropanol. In some typical embodiments, the lower aliphatic alcohol includes methanol and ethanol.

In some embodiments, concentration of the lower aliphatic alcohol in the solvent used for the process of repeatedly crystallizing is 20%-70%. In some typical embodiments, the concentration of the lower aliphatic alcohol in the solvent used for the repeated crystallization process is 30%-60%.

In some embodiments, a material-liquid ratio of the concentrated crude product to the solvent used for repeated crystallization is 1:3-10. In some typical embodiments, the material-liquid ratio of the concentrated crude product to the solvent used for repeated crystallization is 1:5-8.

In some embodiments, the material-liquid ratio of the primary crystallization substance to the solvent used for repeated crystallization is 1:5-10. In some typical embodiments, the material-liquid ratio of the primary crystallization substance to the solvent used for repeated crystallization is 1:6-9.

The present disclosure further provides dihydroquercetin prepared by the preparation method.

BRIEF DESCRIPTION OF DRAWINGS

In order to more clearly illustrate technical solutions of embodiments and examples of the present disclosure, accompanying drawings which need to be used for the embodiments and examples will be introduced briefly below. It should be understood that the accompanying drawings below merely show some embodiments and examples of the present disclosure, and therefore should not be considered as limitation on the scope. A person ordinarily skilled in the art still could obtain other relevant accompanying drawings according to these accompanying drawings, without using creative efforts.

FIGS. 1A-1B show a liquid chromatogram of a semi-synthetic concentrated crude product of dihydroquercetin in Example 2 of the present disclosure;

FIGS. 2A-2B show a liquid chromatogram of a primary crystallization sample of dihydroquercetin in Example 2 of the present disclosure;

FIGS. 3A-3B show a liquid chromatogram of a secondary crystallization sample of dihydroquercetin in Example 2 of the present disclosure;

FIGS. 4A-4B show a liquid chromatogram of a semi-synthetic concentrated crude product of dihydroquercetin in Comparative Example 1 of the present disclosure;

DETAILED DESCRIPTION OF EMBODIMENTS

Figure 1A:
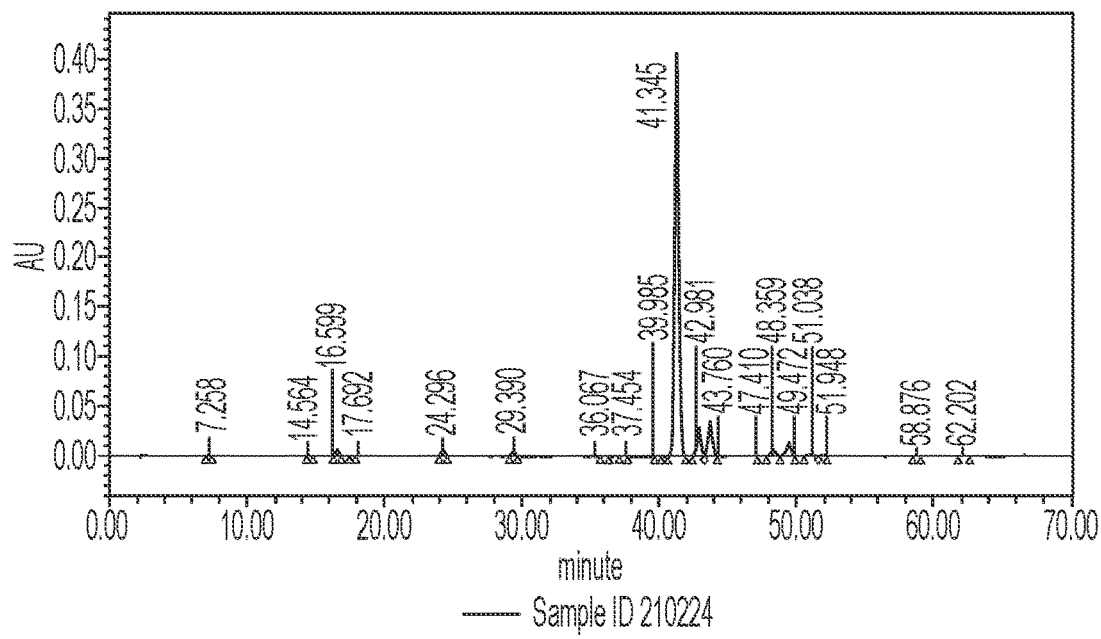

The implementation solutions of the present disclosure will be described in detail below with reference to embodiments and examples, while those skilled in the art could understand that the following embodiments and examples are merely used for illustrating the present disclosure, but should not be considered as limitation to the scope of the present disclosure. If no specific conditions are specified in the embodiments and examples, they are carried out under normal conditions or conditions recommended by the manufacturers. If manufacturers of reagents or apparatuses used are not specified, they are conventional products commercially available.

The preparation route of semi-synthetic dihydroquercetin with quercetin as a raw material has economic advantages and environmental advantages, and particularly can render a target product with trans configuration consistent with that of natural dihydroquercetin. This is a necessary condition for a dihydroquercetin product to enter the pharmaceutical and food fields; however, whether the semi-synthetic method is feasible and economical depends on whether the acid-base property of the reaction solvent, reagent, and reaction medium coincides with advantageous dissolution behavior of quercetin.

Since the quercetin is insoluble in water, and is slightly soluble in solvents such as lower aliphatic alcohols, aliphatic ketones, and fatty acid esters at room temperature (the solubility is less than 1% even in boiling glacial acetic acid), in terms of economy and practicality, neutral or acidic water and most neutral and/or acidic organic solvents are not suitable as semi-synthetic reaction solvents. Therefore, the inventors wish to be capable of implementing and completing the reduction reaction of quercetin in an alkaline aqueous solution. However, it is indeed not easy to find a reduction reaction reagent capable of successfully reducing C ring double bond in a flavonol molecular structure in an alkaline aqueous solution.

After careful design and a large number of experimental researches by the inventors, the present disclosure provides a novel preparation method for reducing quercetin dihydrate (or anhydrous quercetin) to dihydroquercetin in an alkaline aqueous solution with a sulfite (oxygen-containing sulfite) binary combined reducing agent with sodium hydrosulfite as a main component.

Some embodiments of the present disclosure provide a preparation method of dihydroquercetin, including the following steps:

adjusting reaction solvent water to be alkaline with an alkalizing reagent, to obtain an alkaline aqueous solution;

dissolving quercetin dihydrate in the alkaline aqueous solution, and adding a sulfite (which also can be called as oxygen-containing sulfite) binary combined reducing agent to carry out reduction reaction, to obtain an endpoint reduction reaction solution;

diluting the endpoint reduction reaction solution with water, and then acidizing, aging, and filtering the resultant to obtain a filtrate and a filter cake;

subjecting the filtrate to extraction, washing, drying, and vacuum concentration to obtain a concentrated crude product; and repeatedly crystallizing the concentrated crude product with an alcohol-water mixed solvent to obtain dihydroquercetin.

In some optional embodiments of the present disclosure, in order to sufficiently improve the utilization rate of the starting raw material and reduce the production costs, in the present disclosure, the filter cake collected after acidification and filtration is recycled after being washed and purified with hot water (for example, purified water or deionized water or distilled water). That is, when the liquid phase purity of the quercetin dihydrate after being washed and purified with hot water is ≥98%, the quercetin dihydrate can be reused as the starting raw material of the preparation method of dihydroquercetin of the present disclosure; and optionally, the hot water is water of 50° C.-100° C. In some typical embodiments, the hot water is water of 65° C.-85° C. In some typical embodiments, the washing lasts for 10-30 min. In some typical embodiments, the washing lasts for 15-25 min.

In some optional embodiments of the present disclosure, a molar ratio of the quercetin dihydrate to the alkalizing reagent is 1:3.5-5.5, for example, 1:3.5, 1:3.8, 1:4.0, 1:4.5, 1:5.0 or 1:5.5. In some typical embodiments, the molar ratio of the quercetin dihydrate to the alkalizing reagent is 1:4.0-5.0.

In some optional embodiments of the present disclosure, the reaction solvent water is salt-free water, including purified water, deionized water, or distilled water. In some optional embodiments of the present disclosure, the reaction solvent water is purified water.

In some optional embodiments of the present disclosure, the mass ratio of the quercetin dihydrate to the reaction solvent water is 1:80-200, for example, 1:80, 1:100, 1:120, 1:140, 1:160, 1:180, 1:200; in some embodiments of the present disclosure, the mass ratio of the quercetin dihydrate to the reaction solvent water may be 1:100-180, and further may be 1:120-160.

In some optional embodiments of the present disclosure, a mass ratio of the reaction solvent water to the dilution water for diluting the endpoint reduction reaction solution is 1:0.1-0.6, such as 1:0.1, 1:0.2, 1:0.3, 1:0.4, 1:0.5, 1:0.6; and optionally, the mass ratio of the reaction solvent water to the dilution water for diluting the endpoint reduction reaction solution is 1:0.2-0.5.

In some optional embodiments of the present disclosure, the molar ratio of the quercetin dihydrate to the sulfite binary combined reducing agent is 1:3-8, for example, 1:3, 1:4, 1:5, 1:6, 1:7 or 1:8; and in some embodiments of the present disclosure, the molar ratio of the quercetin dihydrate to the sulfite binary combined reducing agent is 1:4.5-7.5, and further may be 1:5.0-6.0.

In some optional embodiments of the present disclosure, the sulfite binary combined reducing agent includes a binary combination of sodium hydrosulfite and sodium pyrosulfite, or a binary combination of sodium hydrosulfite and sodium bisulfite; in some optional embodiments of the present disclosure, the sulfite binary combined reducing agent includes a binary combination of sodium hydrosulfite and sodium pyrosulfite; when the sulfite binary combined reducing agent is a binary combination of sodium hydrosulfite and sodium pyrosulfite, the molar ratio of the sodium hydrosulfite to the sodium pyrosulfite is 1:0.15-0.45, for example, 1:0.15, 1:0.2, 1:0.25, 1:0.3, 1:0.35, 1:0.4 or 1:0.45. In some typical embodiments, the molar ratio of the sodium hydrosulfite to the sodium pyrosulfite is 1:0.2-0.40. In some more typical embodiments, the molar ratio of the sodium hydrosulfite to the sodium pyrosulfite is 1:0.25-0.35.

The combined use of the sodium hydrosulfite and the sodium pyrosulfite or sodium bisulfite in the present disclosure can strongly suppress the production of by-products in the reduction reaction process, compared with the use of sodium hydrosulfite alone; although having the strongest reduction capability among all sulfites, the sodium hydrosulfite still has certain oxidability under certain conditions, and this tendency is particularly evident when the sodium hydrosulfite is used alone as the reducing agent. Under the condition of strong alkalinity (such as pH≥0.0) and high reaction temperatures (for example, the temperature is ≥90° C.), the sodium hydrosulfite will show oxidability more obviously, and further more undesired by-products will be produced; and when the alkalinity is weak or the reaction temperature is low, the reaction yield will decrease obviously. Therefore, in order to minimize the adverse effect of the oxidation tendency of sodium hydrosulfite, the sodium hydrosulfite and the sodium pyrosulfite or sodium bisulfite are compounded (combined) in an appropriate ratio in the present disclosure.

In some optional embodiments of the present disclosure, a reaction temperature of the reduction reaction is 60-120° C., for example, 60° C., 65° C., 70° C., 75° C., 80° C., 85° C., 90° C., 95° C., 100° C., 110° C. or 120° C. In some typical embodiments, the reaction temperature of the reduction reaction is 80-100° C. Reaction time of the reduction reaction is 55-115 min, for example, 55 min, 60 min, 70 min, 80 min, 90 min, 100 min, 110 min or 115 min. In some typical embodiments, the reaction time of the reduction reaction is 70-100 min.

In some optional embodiments of the present disclosure, the extraction solvent is a hydrophobic organic solvent. Optionally, the hydrophobic organic solvent includes at least one of an aliphatic ether, an alicyclic ether, an aliphatic ester, and a hydrophobic aliphatic ketone. Optionally, the hydrophobic organic solvent includes at least one of an aliphatic ether, an aliphatic ester, and a hydrophobic aliphatic ketone. More optionally, the hydrophobic organic solvent includes at least one of isopropyl ether, tert-butyl ether, ethyl acetate, isopropyl acetate, and methyl isobutyl ketone. In some optional embodiments of the present disclosure, a mass ratio of the acidic filtrate after the reduction reaction to the above hydrophobic organic solvent is 1:0.2-0.6, and they are extracted in 3 times according to a conventional method.

In some optional embodiments of the present disclosure, after the 3 times of extraction is completed, the extract solutions are combined, and washed with purified water and an aqueous sodium chloride solution in sequence to remove salt and separate and remove a possible emulsified layer, that is, the combined extracted solutions are first washed once with purified water (corresponding to a batch feeding amount of 20.0 g of quercetin dihydrate, and a water amount herein being 300-500 ml), then washed once with 15% aqueous sodium chloride solution (corresponding to a batch feeding amount of 20.0 g of quercetin dihydrate, and a use amount of the aqueous sodium chloride solution herein being 200-300 ml). After the washing is finished and water layer is separated completely, a drying agent is added to an organic phase for drying and dehydration for 2-3 hours), and after the water-absorbing drying agent is filtered, a dried extract solution is obtained; the drying agent may be anhydrous sodium sulfate, anhydrous magnesium sulfate, anhydrous copper sulfate, anhydrous calcium chloride, molecular sieves, or the like. The dehydrated extract solution is subjected to vacuum concentration, wherein temperature of the concentration may be 50-70° C., and degree of vacuum may be 650-750 mmHg.

In some optional embodiments of the present disclosure, a concentrated crude product is obtained after the above extraction, washing, drying, and vacuum concentration; at this point, the liquid phase purity of the concentrated crude product under normal reaction conditions is about 80% (at least ≥75%). In order to substantially improve the liquid phase purity thereof, the above crude product is repeatedly crystallized in a mixed solvent of a lower aliphatic alcohol and purified water in the present disclosure. In practical operations of the present disclosure, the semi-synthetic dihydroquercetin crude product is added to a round bottom flask, after a solvent for repeated crystallization (re crystallization) is added, the mixture is heated in a water bath and stirred until fully dissolved, then activated carbon is added to reflux and decolorize for about 10 min, the resultant is filtered while it is hot; the collected filtrate is transferred into a crystallization flask, and cooled to 10-5° C. while being slowly stirred, after standing for crystallization, the resultant is subjected to vacuum filtration, and the filter cake is washed 2-3 times with a cold solvent with the same concentration, then subjected to vacuum drying to dry, to obtain a dihydroquercetin primary crystallization substance; after appropriately adjusting the concentration and the ratio of the solvent on the basis of primary recrystallization condition, the dihydroquercetin primary crystallization substance is subjected to secondary crystallization to obtain a dihydroquercetin secondary crystallization substance, i.e. dihydroquercetin with a liquid phase purity of 99.0%.

In order to facilitate those skilled in the art to repeat the method of the present disclosure, the use amount and composition of the solvent for repeated crystallization is illustrated below.

(1) The solvent for repeated crystallization may be a mixed solvent of water and a lower aliphatic alcohol such as methanol, ethanol, and isopropanol. Typically, the lower aliphatic alcohol is methanol and ethanol. The concentration of the lower aliphatic alcohol in the solvent for repeated crystallization is 20%-70% (v/v, the same below). Typically, the concentration of the lower aliphatic alcohol in the solvent for repeated crystallization is 30%-60%, such as 30%, 40%, 50% or 60%.

(2) A material-liquid ratio of the concentrated crude product to the solvent for repeated crystallization is 1:3-10. Typically, the material-liquid ratio of the concentrated crude product to the solvent for repeated crystallization is 1:5-8.

(3) The material-liquid ratio of the dihydroquercetin primary crystallization substance to the solvent for repeated crystallization is 1:5-10. Typically, the material-liquid ratio of the dihydroquercetin primary crystallization substance to the solvent for repeated crystallization is 1:6-9.

In some optional embodiments of the present disclosure, the acidification refers to acidizing, with a dilute acid, the endpoint reduction reaction solution diluted with water; the dilute acid may be dilute hydrochloric acid, dilute sulfuric acid, or dilute acetic acid, etc.; in the illustration in the following embodiments of the present disclosure, the dilute sulfuric acid with a mass concentration of 5%-15% is used; without doubt, the concentration also may be any concentration in the range of 5%-15%, such as 7%, 8%, 9%, 10%, 11%, 12%, and 13%. A pH value of the acidification endpoint is 0.5-4.0, and typically, the pH value is 1.5-3.0. A solution temperature in the acidizing process is 0-35° C., and typically, the temperature is 15-25° C.

Implementation solutions of the present disclosure will be described in detail below with reference to examples, while those skilled in the art would understand that the following examples are merely used for illustrating the present disclosure, but should not be considered as limitation to the scope of the present disclosure. If no specific conditions are specified in the examples, they are carried out under normal conditions or conditions recommended by manufacturers. If manufacturers of reagents or apparatuses used are not specified, they are conventional products commercially available.

The preparation method of dihydroquercetin of the present disclosure is illustrated below.

The preparation method of dihydroquercetin of the present disclosure mainly includes the following steps:

step 1: adjusting reaction solvent water to be alkaline with an alkalizing reagent, to obtain an alkaline aqueous solution; dissolving quercetin dihydrate in the alkaline aqueous solution, and adding a sulfite binary combined reducing agent to carry out reduction reaction, to obtain an endpoint reduction reaction solution;

step 2: diluting the endpoint reduction reaction solution with water, and then acidizing, aging, and filtering the resultant to obtain a filtrate and a filter cake;

step 3: subjecting the filtrate to extraction, washing, drying, and vacuum concentration to obtain a concentrated crude product; and repeatedly crystallizing the concentrated crude product to obtain dihydroquercetin.

In the above step 1, the reaction temperature of the reduction reaction is 60-120° C., and also may be 80-100° C.; and the reaction time of the reduction reaction is 55-115 min, and also may be 70-100 min.

In the above step 2, the dilute acid used in the acidification (ring closing) may be dilute hydrochloric acid, dilute sulfuric acid, or dilute acetic acid, etc.; in the illustration in the following examples of the present disclosure, the dilute sulfuric acid with a mass concentration of 5%-15% is used; without doubt, the mass concentration also may be 8%-12%. A pH value of the acidification endpoint is 0.5-4.0, and also may be 1.5-3.0. A temperature of the reaction solution in the acidizing process should be maintained in 0-35° C., optionally 15-25° C.

In the above step 3, the extraction refers to extracting by shaking the acidified filtrate in 3 times by using a hydrophobic organic solvent, wherein a mass ratio of the acidified filtrate to the hydrophobic organic solvent is 1:0.1-1:1.0. Without doubt, a mixing mass ratio of the acidified filtrate to the hydrophobic organic solvent also may be 1:0.2-1:0.6. In order to facilitate those skilled in the art to better repeat the method of the present disclosure, the hydrophobic organic solvent is illustrated below. The hydrophobic organic solvent may be any one of an aliphatic ether, an aliphatic ester, and/or a hydrophobic aliphatic ketone, such as isopropyl ether, tert-butyl ether, ethyl acetate, isopropyl acetate, and methyl isobutyl ketone.

After 3 times of extraction in the above, extract solutions are combined and then washed.

That is to say, firstly, the extract solutions are washed once with 300-500 ml of purified water, and then washed once with 200-300 ml of 15% aqueous sodium chloride solution. After the washing is finished, a drying agent is added to the organic phase for drying and dehydration, and after the water-absorbing drying agent is filtered, a dehydrated extract solution is obtained; the drying agent may be anhydrous sodium sulfate, anhydrous magnesium sulfate, anhydrous copper sulfate, anhydrous calcium chloride, molecular sieves, or the like. The dehydrated extract solution is concentrated, wherein temperature of the concentration may be 50-70° C., and degree of vacuum may be 650-750 mmHg.

After the above extraction, washing, drying, and concentration, a semi-synthetic crude product of dihydroquercetin can be obtained, at this point, the liquid phase purity of the concentrated crude product obtained under the reduction reaction conditions shown in Table 3 and the test conditions specified in subsequent step 1 to step 3 is about 80%. On this basis, in order to rapidly, conveniently, and substantially improve the liquid phase purity of such crude product to a level of 95% or 99% or higher, through in-depth experimental researches, the inventors designed the technical solution in which two times of recrystallization is carried out by using the lower aliphatic alcohol-purified water mixed solvent as described below. In practical operations of the present disclosure, the semi-synthetic dihydroquercetin crude product is added to a round bottom flask, after the solvent for repeated crystallization is added, the mixture is heated in a water bath and stirred until fully dissolved, then activated carbon is added to reflux and decolorize, the resultant is filtered while it is hot; the collected filtrate is transferred into a crystallization flask, and cooled to 8-2° C. while being slowly stirred, after standing for crystallization for a specified period of time, the resultant is subjected to vacuum filtration, and the filter cake is washed 2-3 times with a cold solvent with the same concentration, then subjected to vacuum drying to dry, to obtain a dihydroquercetin primary crystallization substance (the liquid phase purity is 95.0%); after appropriately adjusting the concentration and the ratio of the solvent on the basis of primary recrystallization condition, the dihydroquercetin primary crystallization substance is subjected to secondary crystallization to obtain a dihydroquercetin secondary crystallization substance, i.e. dihydroquercetin with a liquid phase purity of ≥99.0%.

Besides, in order to improve the utilization rate of the raw materials, the present disclosure further provides an additional step, that is, recycling the filter cake obtained in step 2, with specific steps as follows.

The filter cake obtained in step 2 (droquercetin dihydrate that is not reacted completely) is collected separately or collectively in a round bottom flask, stirred and washed in hot water of 60-100° C. for 10-30 min, so that the dihydroquercetin and other water soluble ingredients contained therein are sufficiently extracted or removed from the filter cake, followed by filtering and drying, so as to improve the purity of quercetin dihydrate to 98% or higher, thus the quercetin dihydrate can be recycled as a starting raw material of the preparation method of the present disclosure.

In order to facilitate those skilled in the art to repeat the method of the present disclosure, the use amount and composition of the solvent for repeated crystallization is illustrated below: (1) the solvent for repeated crystallization may be a mixed solvent of purified water and a lower aliphatic alcohol such as methanol, ethanol, or isopropanol; the lower aliphatic alcohol is optionally methanol and ethanol; and the concentration of the lower aliphatic alcohol in the solvent for repeated crystallization is 20%-70%, optionally 30%-60%, such as 30%, 40%, 50% or 60%; (2) a material-liquid ratio of the concentrated crude product to the solvent for repeated crystallization is 1:3-10, optionally 1:5-8; and (3) a material-liquid ratio of the dihydroquercetin primary crystallization substance to the solvent used for repeated crystallization is 1:5-10, optionally 1:6-9.

A semi-synthetic route of the dihydroquercetin of the present disclosure is as follows:

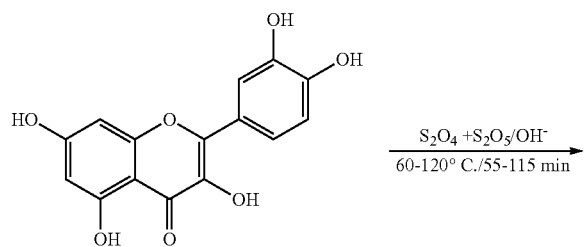

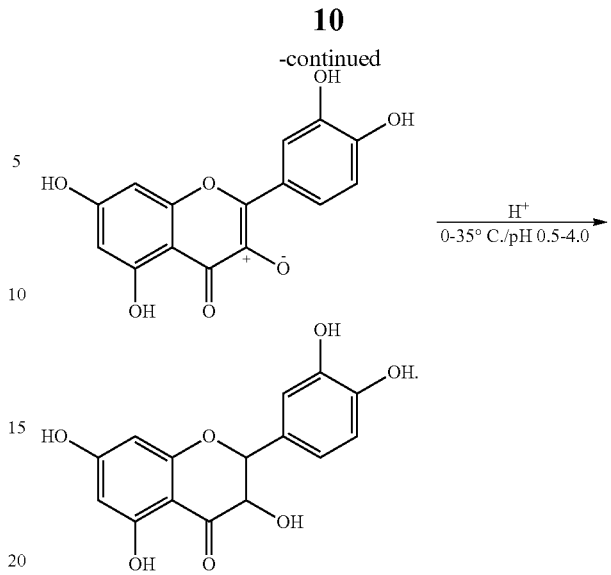

The present disclosure differs from the prior art mainly in different reducing agent, reaction solvent, pH environment of reaction medium, and repeated crystallization method. In the above, the combined use of the reducing agent sodium hydrosulfite and sodium pyrosulfite in a certain proportion is one of the main inventive points of the present disclosure.

A special advantage of the preparation method (semi-synthetic method) of dihydroquercetin of the present disclosure is that it can render dihydroquercetin with trans configuration nearly 100% consistent with that of natural dihydroquercetin.

The reducing agent used in the present disclosure is the sulfite binary combined reducing agent, main component is sodium hydrosulfite, such as a binary combination of sodium hydrosulfite and sodium pyrosulfite or sodium hydrosulfite and sodium bisulfite, or a binary combination of sodium hydrosulfite and other sulfites. The inventors have found through researches that, on the premise that other reduction reaction conditions remain unchanged, when the sodium hydrosulfite alone is used as the reducing agent in place of the binary combined reducing agent of the present disclosure, compared with the latter, the target product dihydroquercetin in the reduced crude product obtained by the former has a very low liquid phase purity (see Comparative Example 1 in Table 4), and there are numerous complex by-products, therefore, there is no further research and industrial practical values; in the above, a structure of a main by-product is as follows:

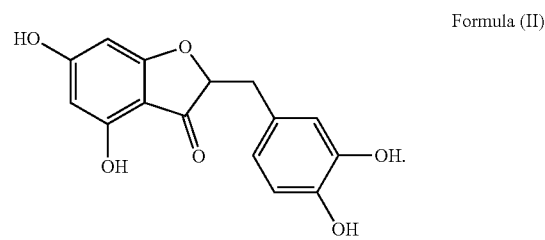 [SMILES: O=C1c2c(O)cc(O)cc2OC1Cc1ccc(O)c(O)c1]

Formula (II)

The polarity of this by-product is quite close to that of the target product (the liquid chromatogram shows that retention time of the two differs by only about 1 min), so that they are not easy to be separated, and more products will be lost during the separation process.

Based on the above reasons, in order to suppress the generation of such by-products to the greatest extent, the inventors have found through in-depth experimental researches that when sodium pyrosulfite or sodium bisulfite is used in combination with sodium hydrosulfite in a certain proportion, the purity of the target product is substantially improved (see Example 1, Example 2, and Example 11 in Table 4), so that the solution of the present disclosure has a relatively high development and application value.

The molar ratio of the sulfite binary combined reducing agent as stated above in the method of the present disclosure is quercetin dehydrate:combined reducing agent=1:3.0-8.0, and without doubt, the molar ratio of the quercetin dihydrate to the combined reducing agent also may be 1:4.5-7.5, and further may be 1:5.0-6.0.

In order to facilitate those skilled in the art to repeat the method of the present disclosure, the combination ratios of various components in the binary combined reducing agent are exemplified below: for example, when the sulfite binary combined reducing agent is a binary combination of sodium hydrosulfite and sodium pyrosulfite, the molar ratio of the two is 1:0.15-0.45, also may be 1:0.2-0.4, and further may be 1:0.25-0.35.

The present disclosure uses the inexpensive alkaline aqueous solution as the reduction reaction solvent for quercetin, and defines the use amount of water, i.e., the mass ratio of the quercetin dihydrate to the water is 1:80-200; optionally, the mass ratio of the quercetin dihydrate to the water is 1:100-180; more optionally, the mass ratio of the quercetin dihydrate to the water is 1:120-160; when the endpoint reduction reaction solution is diluted with water, the mass ratio of the reaction solvent water to the dilution water is 1:0.1-0.6, and more optionally, the mass ratio of the reaction solvent water to the dilution water is 1:0.2-0.5.

Compared with neutral and acidic organic solvents, water is used as a basic solvent in the present disclosure, after it is adjusted to be alkaline with an alkalizing reagent, a semi-synthetic reaction of quercetin is implemented and completed by using the sulfite binary combined reducing agent in the present disclosure, and the use amount of the alkalizing reagent is defined, i.e. the molar ratio of the quercetin dihydrate to the alkalizing reagent in step 1 is 1:3.5-5.5, optionally 1:4.0-5.0; and a range of the pH value of the reaction medium from the start to the end of the reduction reaction is 7.0-13.0, optionally 7.5-12.5.

In the present disclosure, after the endpoint reduction reaction solution is acidified with dilute acid to be acidic, unreacted quercetin chalcone is made to close the ring again (regenerated quercetin), and sufficiently precipitates from the aqueous phase system rapidly. After aging for a certain period of time, the resultant is sufficiently separated from the main reaction product (i.e., dihydroquercetin, soluable in an acidic aqueous solution) in the simplest way of filtration (liquid-solid separation). The above-mentioned separation method is based on the property difference that the quercetin (or dihydrate) is soluble in an alkaline aqueous solution (open ring), and is almost insoluble in an acidic aqueous solution (close ring), while the dihydroquercetin is soluble in both alkaline and acidic aqueous solutions, thus, it is designed that after the endpoint reduction reaction solution is first diluted with a proportional amount of dilution water and cooled to room temperature, it is directly acidified with dilute acid to a specified pH value, then the unreacted quercetin dihydrate (the starting raw material) sufficiently precipitates from the mixed system, and the resultant dihydroquercetin remains in the aqueous phase. After aging (standing) for a certain period of time, precipitate is filtered out (cut-off) from the acidified substance by using double-layer filter paper or a No. 2 sand filter, so as to easily realize sufficient separation of the resultant from the non-acting substances sufficiently.

In order to sufficiently recycle such valuable waste resources, the applicant innovatively developed that in the present disclosure, the above filter cake (quercetin dihydrate precipitate) obtained by filtration is poured into a beaker, to which a specified amount of purified water pre-heated to a specified temperature is added, the mixture is continuously stirred and washed under heat preservation condition for an appropriate period of time, and then the washing solvent is filtered out. The resulting filter cake has a liquid phase purity of ≥99%. The recycled by-products with such purity completely meet the quality requirement of recycling.

A conventional method for separating a single flavone ingredient from a bioflavonoid mixture is known to be chromatographic column separation or macroporous resin adsorption separation method. Although the separation effect is good, the separation cycle is long, and particularly, the polyamide or macroporous resin used needs a relatively long regeneration treatment process. As an industrial production method, it apparently lacks economy, and it is difficult to achieve large-scale production. With a view to future industrial production, the present applicant has proposed such an economical, convenient, and time-saving method of two times of recrystallization with a mixed solvent of a lower aliphatic alcohol and purified water, which can rapidly increase the purity of the semi-synthetic dihydroquercetin crude product having a liquid phase purity of about 80% to a 99.5% high-purity dihydroquercetin product. The dihydroquercetin industrial grade product with the liquid phase purity of 90-95%, in greater demand currently in the market, can be easily obtained by only one recrystallization process.

The lower aliphatic alcohol includes at least one of methanol, ethanol, and isopropanol, and optionally, the lower aliphatic alcohol includes methanol and ethanol; and considering the problem of use safety of methanol, the present disclosure optionally uses ethanol. In the solvent for repeated crystallization, concentration of the lower aliphatic alcohol ranges 20%-70%, optionally 30%-60%.

The liquid chromatography conditions for measuring the liquid phase purity of the reduction reaction crude product and the primary and secondary crystallization substances in the two recrystallization processes in the present disclosure are as follows:

chromatography column: Intertsustain C18, 250*4.6, 5 μm, CN-6020-07346, S/N5JR98073;

mobile phase: A pump 0.1% phosphoric acid aqueous solution, B pump-methanol;

gradient method: flow rate of 1.5 ml/min, sampling size of 10 μL, column temperature of 40° C., detection wavelength of 290 nm; and concentration of sample for test: 0.5 mg/ml.

The preparation method of dihydroquercetin in the present disclosure is further described in detail below in conjunction with the examples.

Information about main instrument used in all the following examples and comparative examples is as shown in Table 1, and information about raw materials, reagents, and solvents used is as shown in Table 2:

TABLE 1

| Instrument name | Model/ Specification | Instrument No. | Manufacturer |
| --- | --- | --- | --- |
| Electronic balance | B3002 | YHA009 | Shanghai Liangping Instrument Company |
| pH-temperature measuring system | M400 | / | METTLER TOLED (Shanghai) Co., Ltd. |
| Constant speed electric mixer | JJ-2Q | / | Changzhou Guoyu Instrument Manufacturing Co., Ltd. |
| Constant temperature Vacuum drying oven | DZF-6050 | B61016 | Shanghai Boxun Experiment Co., Ltd. |

TABLE 1-continued

| Instrument name | Model/ Specification | Instrument No. | Manufacturer |
|---|---|---|---|
| Vacuum filter | 1000 ml × 500 ml | / | Shanghai Glass Instrument Co., Ltd. |

TABLE 2

| Name | Specification | Purity/content | Manufacturer |
|---|---|---|---|
| Quercetin dihydrate | Pharmaceutical grade | Content ≥95% | Shaanxi Jiahe Phytochem Co., Ltd. |
| Sodium hydrosulfite | Analytically pure | Content ≥88.0% | Macklin Company |
| Sodium pyrosulfite | Analytically pure | Content ≥99.0% | Macklin Company |
| Sodium bisulfite | Analytically pure | Content ≥99.0% | Macklin Company |
| Anhydrous sodium carbonate | Analytically pure | Content ≥99.0% | Sinopharm Shanghai Chemical Reagent Co., Ltd. |
| Purified water | Meet GMP standards | / | Enterprise self-made |
| Ethanol | Pharmaceutical grade | Contents ≥95% | Xuzhou Xiangpei |
| Isopropyl acetate | Industrial premium product | Contents ≥99% | Sinopharm Shanghai Chemical Reagent Co., Ltd. |
| Sulfuric acid | Reagent grade | Content 95-98% | Yangzhou Hubao Chemical Reagent Co., Ltd. |
| Sodium chloride | Reagent grade | Content ≥99.0% | Sinopharm Shanghai Chemical Reagent Co., Ltd. |
| Activated carbon | Pharmaceutical grade | Content: 99.9% | Shanghai Activated Carbon Co., Ltd. |

In the present disclosure, the molar ratio of the quercetin dihydrate ("starting raw material" for short in Table 3) to the binary combined reducing agent ("reducing agent" for short in Table 3), the molar ratio of the sodium hydrosulfite ("A" for short in Table 3) to the sodium pyrosulfite ("B" for short in Table 3) or the sodium bisulfite ("C" for short in Table 3) in the binary combined reducing agent, the reaction temperature and reaction time of the reduction reaction are variable parameters, and they are arranged in corresponding positions of various examples and comparative examples in Table 3.

TABLE 3

| Implementation No. | Starting raw material/ reducing agent (by molar ratio) | Composition of reducing agent (by molar ratio) | Reaction temperature (° C.) | Reaction time (min) |
|---|---|---|---|---|
| Example 1 | 1:5.5 | A:B = 1:0.274 | 90-100 | 75-80 |
| Example 2 | 1:5.5 | A:B = 1:0.274 | 90-100 | 75-80 |
| Example 3 | 1:3.85 | A:B = 1:0.274 | 90-100 | 75-80 |
| Example 4 | 1:7.15 | A:B = 1:0.274 | 90-100 | 75-80 |
| Example 5 | 1:5.5 | A:B = 1:0.192 | 90-100 | 75-80 |
| Example 6 | 1:5.5 | A:B = 1:0.356 | 90-100 | 75-80 |
| Example 7 | 1:5.5 | A:B = 1:0.274 | 80-90 | 75-80 |
| Example 8 | 1:5.5 | A:B = 1:0.274 | 100-110 | 75-85 |
| Example 9 | 1:5.5 | A:B = 1:0.274 | 90-100 | 65-70 |
| Example 10 | 1:5.5 | A:B = 1:0.274 | 90-100 | 85-90 |
| Example 11 | 1:6.45 | A:C = 1:0.274 | 85-95 | 80-85 |
| Comparative Example 1 | 1:5.5 | Only a single component A | 90-100 | 75-80 |
| Comparative Example 2 | 1:5.5 | Only a single component B | 90-100 | 75-80 |
| Comparative Example 3 | 1:6.45 | Only a single component C | 85-95 | 80-85 |

Note: In the above table, Example 2 is an example in which Example 1 is magnified by 5 times (mass ratio).

The fixed process conditions, parameters, and preparation procedures in the dihydroquercetin preparation process in various examples and comparative examples in Table 3 are as follows.

Step 1: Reduction Reaction 3000 ml of purified water and 24.5 g of sodium carbonate were added to a reaction bottle, the mixture was continuously stirred until pH was stable, and then heated in a water bath to 50-55° C., and 20 g of quercetin dihydrate was added; the resultant continued to be heated until reaching the reaction temperature specified in various examples and comparative examples, a specified amount of the combined (or single) reducing agent in various examples was added for reduction reaction, and after continuous stirring and reaction proceeded to specified end time, 750 ml of purified water pre-cooled to 5° C. or lower was rapidly added to dilute the reaction solution, so as to stop the reaction and obtain the endpoint reduction reaction solution.

Step 2: Acidizing, Aging, and Filtering

After being cooled to room temperature, the endpoint reduction reaction solution obtained in step 1 was acidified with 10% dilute sulfuric acid uniformly added dropwise while stirring to a pH value of 2.0-2.5, and the resultant stood and was aged for 2.5 h, and then filtered, to obtain a clear acidic filtrate containing dihydroquercetin, which stood for later use.

P.S.: Washing and Purifying the Filter Cake

The filter cakes recycled in each batch were combined in a beaker, 80° C. hot purified water 10 times the mass was added, followed by stirring and washing in a 80-85° C. water bath for 20 min, then the resultant was filtered while it was hot, then the filter cakes were washed twice with hot purified water 5 times the mass, after filtering the filter cakes, the filter cake was dried by air-blast drying in an air-blast drying cabinet to dry. A sample was taken and detected for liquid phase purity thereof. When the purity thereof was 98%, it could be recycled as a starting raw material for the present semi-synthetic reaction.

Step 3: Extracting, Washing, Drying, and Concentrating

The acidic filtrate containing dihydroquercetin obtained in step 2 was extracted by shaking in 3 times (500+350+300 ml) with 1150 ml of isopropyl acetate, the extract solutions were combined, washed once with 350 ml of purified water, and then washed once with 250 ml of 15% aqueous sodium chloride solution; after water layer and possible emulsified layer were separated completely, 35 g of anhydrous sodium sulfate was added for stirring and washing for 5 min, then the resultant stood to dehydrate for 2.5 h, and after sodium sulfate was filtered off, a dehydrated extract solution was obtained; the extract solution was concentrated in a water bath at a temperature of 50-70° C. and a vacuum degree of 650-750 mmHg until no droplets dripped out and then undergone vacuum dry for 30 min to obtain a light-amber honeycomb semi-synthetic dihydroquercetin concentrated crude product, which was collected and sampled for liquid phase detection.

Step 4: Repeated Crystallization

1) Primary Recrystallization

To a round bottom flask with a condenser a specified amount of the semi-synthetic concentrated crude product of dihydroquercetin obtained in step 3 and an ethanol-water mixed solvent 6.5 times the mass with an ethanol concentration of 40% were added, the mixture was heated in a water bath and stirred until fully dissolved, activated carbon equivalent to 0.5% of the mass of the crude product was added to reflux and decolorize for 10 min, the resultant was filtered while it was hot, the filter cake was washed twice (10 ml+5 ml) with 15 ml of a hot solvent with the same concentration, the filtrate and washing liquid were combined, and transferred into a crystallization flask, cooled to 8° C. or lower while being slowly stirred, and after being allowed to stand and crystallize at 8-3° C. for 2 h, vacuum filtration was carried out, the filter cake was washed twice (10 ml+7 ml) with a cold solvent precooled to 5° C. or lower, and was subjected to vacuum drying at 60° C. or lower to dry after draining, to obtain a dihydroquercetin primary crystallization substance;

2) Secondary Crystallization

A specified amount of primary crystallization substance was placed in a round bottle flask, an ethanol-water mixed solvent 8.0 times the mass of the primary crystallization substance with an ethanol concentration of 50% was added, and then the mixture was subjected to dissolving, decolorizing, filtering, cooling and crystallization, filtering, and vacuum drying in sequence according to the method of primary crystallization, to obtain a dihydroquercetin secondary crystallization substance with a liquid phase purity of ≥99%.

2) Under the conditions of the same reaction temperature and the same reaction time, as the molar ratios of the starting raw material to the reducing agent in Example 1, Example 2 (amplified verification example of Example 1, the same below), Example 3, and Example 4 are different, the reduction reaction yield and the target product purity (corresponding indexes are the maximum single impurity and the total impurity area percentage, the same below) of Examples 1 and 2 are obviously higher than those in Examples 3 and 4. In Examples 5 and 6, the molar ratio between the components A and B in the combined reducing agent (A+B) of Example 1 is moderately changed, and it can be seen that Example 1 has higher reduction reaction yield and higher purity of the target product than those in Examples 5 and 6.

3) Examples 7-10 are experimental results after cross change of reaction temperature and time, and the data show that: compared with Examples 3-4 (molar ratio change), the

TABLE 4

Experimental Results under Reduction Reaction Conditions in Various Examples and Comparative Examples in Table 3

| Implementation No. | Concentrated crude product output | Pure yield of reduction reaction | Liquid phase purity of concentrated crude product | Recycling amount of quercetin dihydrate | Recycling rate of quercetin dihydrate | Total number of impurities | Maximum single impurity area percentage | Total impurity area percentage |
|---|---|---|---|---|---|---|---|---|
| Example 1 | 15.84 g | 85.88% | 79.97% | 2.75 g | 13.75% | 18 | 5.77% | 20.03% |
| Example 2 | 79.26 g | 86.81% | 80.58% | 13.96 g | 13.96% | 18 | 5.81% | 19.42% |
| Example 3 | 12.06 g | 67.54% | 66.51% | 6.11 g | 30.55% | 17 | 5.31% | 33.49% |
| Example 4 | 16.41 g | 59.91% | 55.19% | 2.32 g | 11.60% | 20 | 10.25% | 44.81% |
| Example 5 | 12.73 g | 68.68% | 64.17% | 6.09 g | 30.45% | 15 | 11.50% | 35.83% |
| Example 6 | 13.29 g | 63.23% | 59.72% | 5.32 g | 26.60% | 19 | 10.46% | 40.28% |
| Example 7 | 15.59 g | 79.99% | 74.41% | 3.04 g | 15.20% | 17 | 5.86% | 25.59% |
| Example 8 | 15.64 g | 74.19% | 69.89% | 2.77 g | 13.85% | 21 | 6.38% | 30.11% |
| Example 9 | 15.53 g | 82.24% | 75.57% | 3.31 g | 16.55% | 18 | 5.58% | 24.43% |
| Example 10 | 15.64 g | 78.95% | 72.64% | 3.17 g | 15.85% | 22 | 6.78% | 27.36% |
| Example 11 | 14.91 g | 76.34% | 71.67% | 3.63 g | 18.15% | 19 | 5.67% | 28.33% |
| Comparative Example 1 | 9.05 g | 44.57% | 46.03% | 9.07 g | 45.35% | 25 | 12.31% | 53.97% |
| Comparative Example 2 | 7.93 g | 26.30% | 29.89% | 9.46 g | 47.30% | 24 | 13.67% | 70.11% |
| Comparative Example 3 | 7.50 g | 19.33% | 23.34% | 9.41 g | 47.05% | 24 | 15.46% | 76.66% |

Notes: The quercetin dihydrate has the molar mass of 338.27, and the content of ≥95.0%, and the molar mass of the dihydroquercetin is 304.25; and it can be seen from the corresponding relation between conditions and results in Table 3 and Table 4 that:

1) The single reducing agents A, B, and C are respectively used in Comparative Examples 1-3 to replace the two binary combined reducing agents A+B and A+C in Example 1 and Example 11. Experimental results of 3 comparative examples clearly show that: the experimental results of using a single reducing agent are quite worse than the results of Examples 1 and 11. The reducing agent used in Comparative Example 1 is the component A, and through comparing with Example 1 (A+B), the result indicates that: only when the reducing agent component A forms a binary combination with B or C component, can the ideal or better or acceptable effects shown in Example 1, Example 2-Example 11 in Table 4 be seen. The results must be terrible when the single component A, B or C is used alone. The superiority of the solution of the present disclosure is justified from the opposite. Obviously, the reduction reaction yield and the liquid phase purity of the concentrated crude product in Examples 1-11 are both significantly higher than those in Comparative Examples 1-3 of the present disclosure.

differences between Examples 7-10 and Example 1 are obviously reduced. Thus, it is indicated that: among many process parameters of the reduction reaction, whether the parameters of molar ratios between the starting raw material and the combined reducing agent and between the two components A and B in the combined reducing agent are properly set is the first and second factors affecting the reaction result.

4) The relevant data results of Example 1 and Example 11 in Table 4 indicate that, when other parameters are fixed, after the component B is replaced by the reducing agent component C (i.e., the binary combination of A+C), the pure yield level and liquid phase purity of the reduction reaction in Example 1 are both obviously improved compared with Example 11, indicating that among the sulfite binary combined reducing agents, the binary combination of A+B can render higher reduction reaction yield and crude product liquid phase purity results than the binary combination of A+C.

TABLE 5

Experimental Results of Primary Recrystallization in Some Representative Examples in Table 4

| Implementation No. | Amount of concentrated crude product input | Liquid phase purity of concentrated crude product input | Primary crystallization substance output | Liquid phase purity of primary crystallization substance | Weight yield of primary crystallization substance | Molar yield of primary crystallization substance |
|---|---|---|---|---|---|---|
| Example 1 | 15.0 g | 79.97% | 11.34 g | 95.89% | 75.60% | 90.65% |
| Example 2 | 74.66 g | 80.58% | 56.75 g | 95.93% | 76.01% | 90.49% |
| Example 5 | 12.5 g | 64.17% | 8.42 g | 79.81% | 67.36% | 83.78% |
| Example 8 | 15.0 g | 69.89% | 10.59 g | 87.12% | 70.60% | 88.01% |
| Comparative Example 1 | 10.0 g | 46.03% | 4.95 g | 62.97% | 49.50% | 67.72% |
| Comparative Example 2 | 7.5 g | 29.87% | 2.40 g | 43.87% | 32.00% | 47.00% |
| Comparative Example 3 | 7.0 g | 24.34% | 1.43 g | 36.63% | 20.43% | 30.74% |

TABLE 6

Experimental Results of Secondary Crystallization of Primary Crystallization Substances in Various Examples and Comparative Examples in Table 5

| Implementation No. | Amount of primary crystallization substance input | Liquid phase purity of primary crystallization substance input | Secondary crystallization substance output | Liquid phase purity of secondary crystallization substance | Yield of secondary crystallization process | Total number of impurities | Total impurity area percentage |
|---|---|---|---|---|---|---|---|
| Example 1 | 11.0 g | 95.58% | 8.89 g | 99.66% | 84.30% | 5 | 0.34% |
| Example 2 | 50.0 g | 95.93% | 40.46 g | 99.64% | 84.27% | 5 | 0.36% |
| Example 5 | 8.0 g | 79.81% | 5.91 g | 87.17% | 80.69% | 7 | 12.83% |
| Example 8 | 10.0 g | 87.12% | 7.45 g | 95.57% | 81.73% | 6 | 4.43% |
| Comparative Example 1 | 4.50 g | 62.97% | 2.24 g | 70.28% | 55.56% | 9 | 29.72% |
| Comparative Example 2 | 2.0 g | 43.87% | 0.75 g | 49.43% | 42.25% | 9 | 50.57% |
| Comparative Example 3 | 1.25 g | 36.63% | 0.39 g | 41.07% | 34.98% | 12 | 58.93% |

The experimental data in Table 5-Table 6 show that when the liquid phase purity of the concentrated crude product (primarily refined raw material) is higher (e.g. Examples 1-2), high-purity dihydroquercetin (secondary crystallization substance) with purity of ≥99.5% can be obtained just by implementing two times of simple recrystallization process. In contrast, when the liquid phase purity of the reduction crude product is lower than 50% (Comparative Examples 1-3), the economic value is obviously lacked.

The test results of repeated crystallization of various examples also indicate that the parameters of alcohol concentration and liquid-solid ratio in the two alcohol-water mixed solvents for repeated crystallization provided in the present disclosure are not only suitable, but also very effective. This greatly improves the efficacy compared with the conventional polyamide column chromatography or macroporous resin adsorption separation method.

Figure 2A:
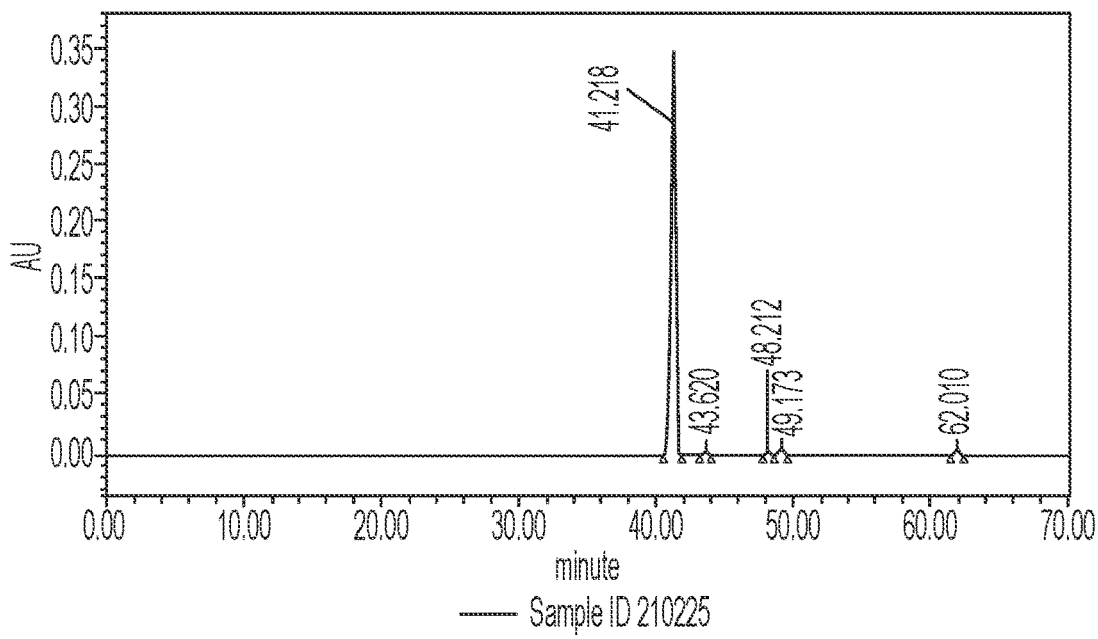
Figure 3A:
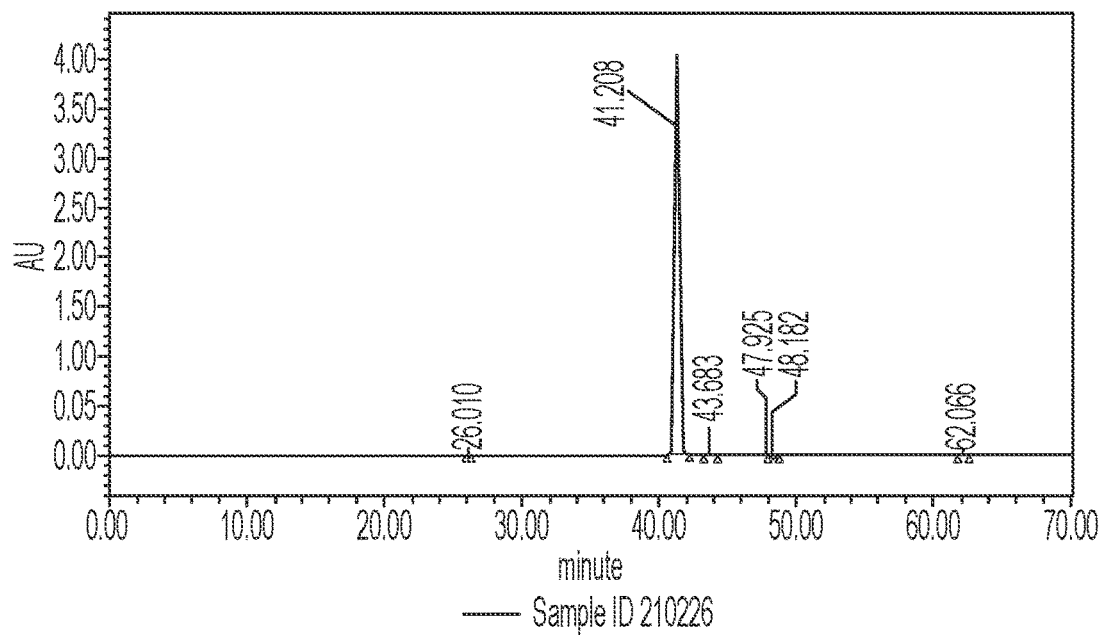
Figure 4A:
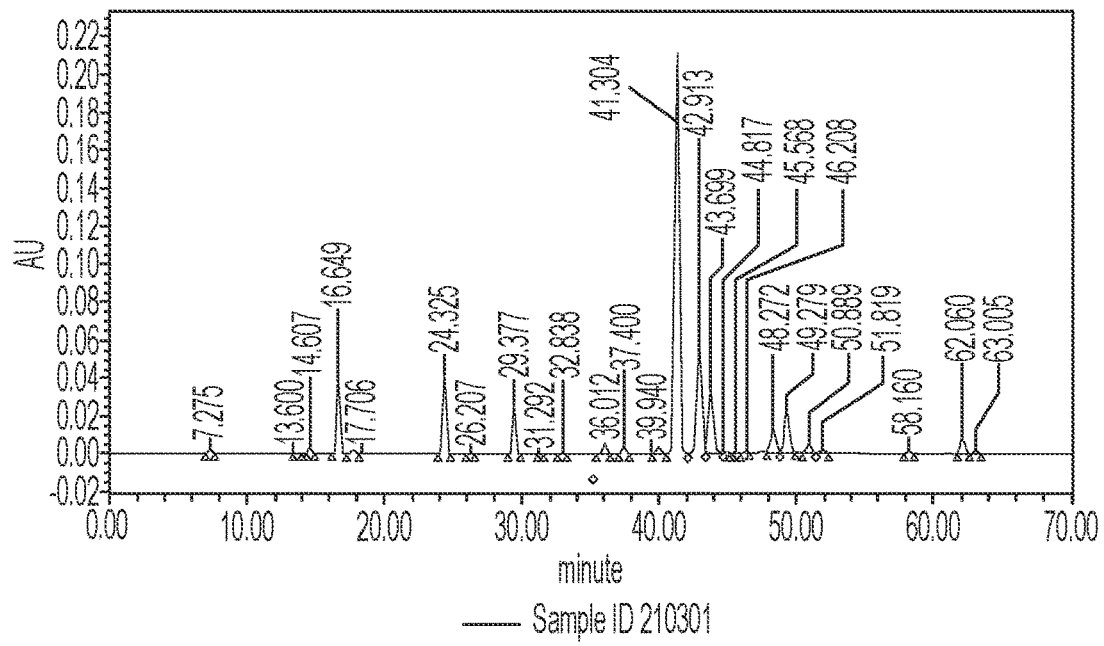
Figure 5:
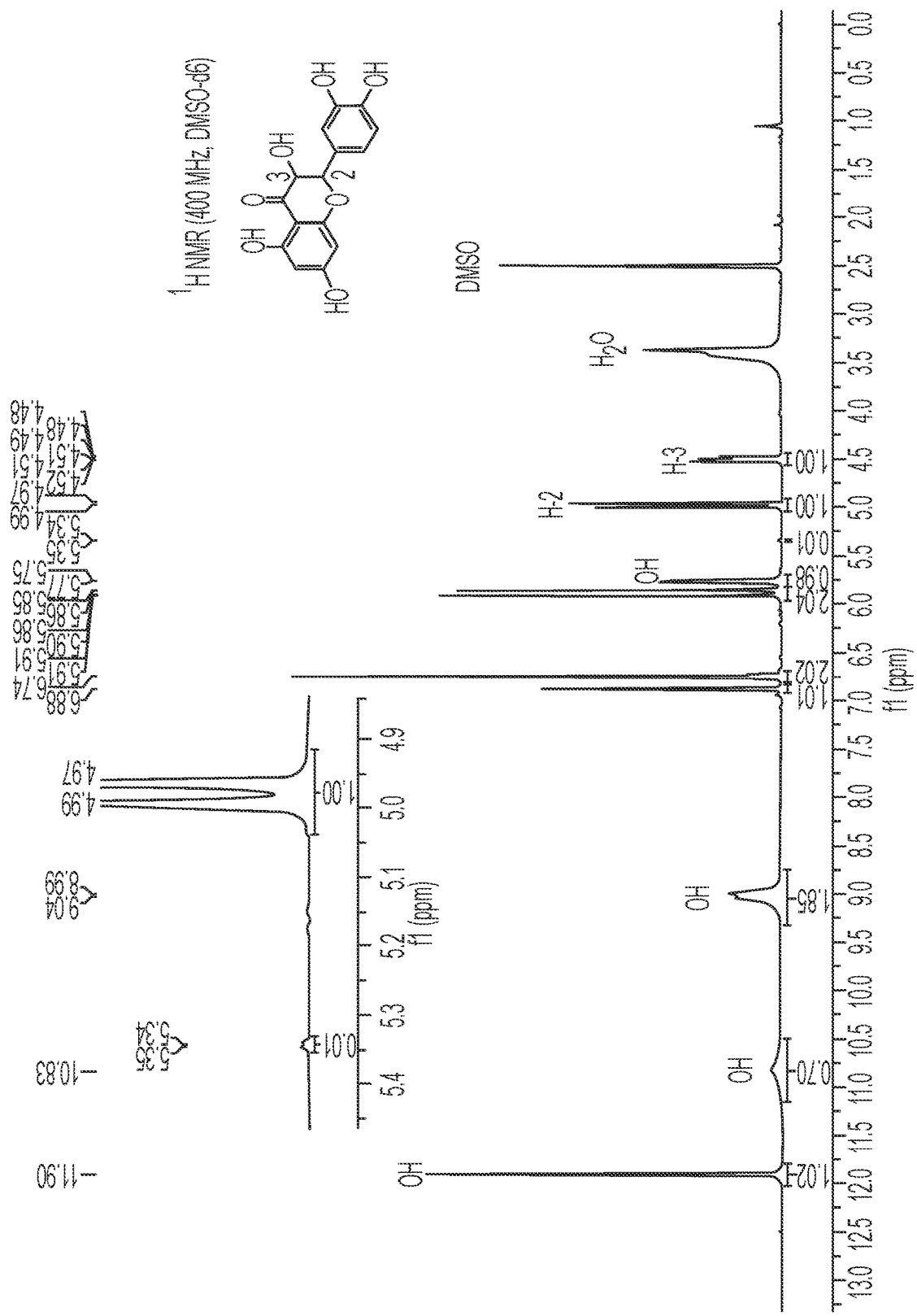
FIG. 5 is a $^1$H NMR spectrum of the secondary crystallization sample of dihydroquercetin in Example 2 of the present disclosure.

In the accompanying drawings, FIG. 1 is a liquid chromatogram of the semi-synthetic concentrated crude product of dihydroquercetin in Example 2 of the present disclosure; FIG. 2 is a liquid chromatogram of the primary crystallization substance (crystallization sample) of dihydroquercetin in Example 2 of the present disclosure; FIG. 3 is a liquid chromatogram of the secondary crystallization substance (crystallization sample) of dihydroquercetin in Example 2 of the present disclosure; FIG. 4 is a liquid chromatogram of the semi-synthetic concentrated crude product of dihydroquercetin in Comparative Example 1 of the present disclosure; and FIG. 5 is a $^1$H NMR spectrum of the secondary crystallization substance (crystallization sample) of dihydroquercetin in Example 2 of the present disclosure.

Analytical results of elements of the secondary crystallization substance ("sample for test" for short below) of Example 2 in Table 6 are as shown in Table 7:

TABLE 7

Results of Element Analysis Test

| Element | C | H | O |
|---|---|---|---|
| Theoretical value | 59.21% | 3.98% | 36.81% |
| Analytical value | 59.20% | 3.98% | 36.80% |

Conclusion: An error range of the analytical value and the theoretical value in Table 7 meets requirements (<±0.3%).

$^1$H NMR spectral data characterization of semi-synthetic dihydroquercetin sample for test in the present disclosure:

$^1$H NMR spectral data characterization is performed by taking the dihydroquercetin secondary crystallization sample prepared in Example 2 of the present disclosure as an example.

Structural formula and ¹H NMR spectral data of the secondary crystallization sample of dihydroquercetin are as follows:

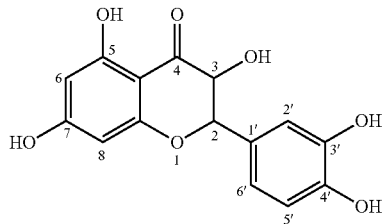

Formula (III)

¹H NMR spectral data: ¹H NMR (400 MHz, DMSO-d6): δ 11.90 (s, 1H, OH-5), 10.83 (b, 1H, OH-7), 9.04 (s, 1H, OH-3'), 8.99 (s, 1H, OH-4'), 6.88 (s, 1H, Ar—H-2'), 6.74 (s, 2H, Ar—H-5',6'), 5.91-5.90 (m, 1H, Ar—H-8), 5.86-5.85 (m, 1H, Ar—H-6), 5.76 (d, J=5.8 Hz, 1H, OH-3), 4.98 (d, J=11.3 Hz, 1H, H-2), 4.52-4.48 (m, 1H, H-3).

¹H NMR characterization data analysis:

According to the ¹H NMR spectrum, hydrogen at sites 2 and 3 of this compound is trans (1:1 mixture of two isomers 2R, 3R and 2S, 3S), because a coupling constant of the two Hs is 11.3 Hz. If the two Hs are cis, the coupling constant should be 2-3 Hz.

According to the ¹H NMR spectrum, the content of cis isomer in the sample is extremely small. H-2 of the cis isomer should show a signal around δ 5.34, which accounts for only about 1% in this spectrum.

Conclusion: the proportion of the trans isomers in the sample for test is about 99%, which is consistent with the trans configuration of natural dihydroquercetin.

Notes: The above ¹H NMR spectrum and analytical result of dihydroquercetin and FIG. 5 are derived from the Department of Chemistry, University of Science and Technology of China.

The above-mentioned are merely for examples of the present disclosure and not intended to limit the present disclosure. For one skilled in the art, various modifications and variations may be made to the present disclosure. Any amendments, equivalent replacements, improvements and so on made within the spirit and principle of the present disclosure should be covered within the scope of protection of the present disclosure.

INDUSTRIAL APPLICABILITY

The present disclosure provides a preparation method of dihydroquercetin. This preparation method has significant advantages of short reaction steps, inexpensive reaction solvent (harmless) and reagent, simple purification process of crude product, fewer pollutants, and low production costs; moreover, the unreacted low-purity starting raw material (filter cake) after the reduction reaction is fully recycled after simple and efficient purification treatment, further reducing the cost of the semi-synthetic raw material; and particularly, in the target product obtained by the present semi-synthetic method, the trans isomers accounts for about 99%, consistent with the trans configuration of natural dihydroquercetin. Therefore, it has very good promotion and application value, and is particularly suitable for large-scale industrial production.

What is claimed is:

1. A preparation method of dihydroquercetin, comprising the steps of:
   adjusting the alkalinity of a water reaction solvent with an alkalizing reagent, to obtain an alkaline aqueous solution;
   dissolving quercetin dihydrate in the alkaline aqueous solution, and adding an oxygen-containing sulfite binary combined reducing agent to carry out reduction reaction, to obtain an endpoint reduction reaction solution;
   diluting the endpoint reduction reaction solution with water, and then acidizing, aging, and filtering a resultant to obtain a filtrate and a filter cake;
   subjecting the filtrate to extraction, washing, drying, and vacuum concentration to obtain a concentrated crude product; and
   repeatedly crystallizing the concentrated crude product to obtain the dihydroquercetin,
   wherein the oxygen-containing sulfite binary combined reducing agent is selected from the group consisting of a binary combination of sodium hydrosulfite and sodium pyrosulfite and a binary combination of sodium hydrosulfite and sodium bisulfite.

2. The preparation method of dihydroquercetin according to claim 1, wherein a mass ratio of the quercetin dihydrate to the water reaction solvent is 1:80-200.

3. The preparation method of dihydroquercetin according to claim 2, wherein the mass ratio of the quercetin dihydrate to the water reaction solvent is 1:100-180.

4. The preparation method of dihydroquercetin according to claim 1, wherein a molar ratio of the quercetin dihydrate to the alkalizing reagent is 1:3.5-5.5.

5. The preparation method of dihydroquercetin according to claim 1, wherein a molar ratio of the quercetin dihydrate to the oxygen-containing sulfite binary combined reducing agent is 1:3-8.

6. The preparation method of dihydroquercetin according to claim 1, wherein the oxygen-containing sulfite binary combined reducing agent is a binary combination of sodium hydrosulfite and sodium pyrosulfite.

7. The preparation method of dihydroquercetin according to claim 6, wherein a molar ratio of the sodium hydrosulfite to the sodium pyrosulfite is 1:0.15-0.45.

8. The preparation method of dihydroquercetin according to claim 1, wherein a reaction temperature of the reduction reaction is 60-120° C., and a reaction time is 55-115 min.

9. The preparation method of dihydroquercetin according to claim 1, wherein a mass ratio of the reaction solvent water to water used for dilution after the reduction reaction is 1:0.1-0.6.

10. The preparation method of dihydroquercetin according to claim 1, wherein the acidizing refers to acidizing, with a dilute acid, the endpoint reduction reaction solution diluted with water.

11. The preparation method of dihydroquercetin according to claim 10, wherein a pH value of the acidified endpoint solution is 0.5-4.0.

12. The preparation method of dihydroquercetin according to claim 10, wherein a solution temperature in the acidizing process is 0-35° C.

13. The preparation method of dihydroquercetin according to claim 1, wherein an extraction solvent used in the extraction is a hydrophobic organic solvent.

14. The preparation method of dihydroquercetin according to claim 13, wherein the hydrophobic organic solvent is at least one selected form the group consisting of an aliphatic ether, an alicyclic ether, an aliphatic ester, and a hydrophobic aliphatic ketone.

15. The preparation method of dihydroquercetin according to claim 1, wherein the process of the repeatedly crystallizing comprises: subjecting the concentrated crude product to primary crystallization to obtain a primary crystallization substance; and crystallizing the primary crystallization substance secondarily to obtain a secondary crystallization substance.

16. The preparation method of dihydroquercetin according to claim 15, wherein the solvent used for the repeated crystallization is a mixed solvent of lower aliphatic alcohol and water.

17. The preparation method of dihydroquercetin according to claim 16, wherein the concentration of the lower aliphatic alcohol in the solvent used for the process of the repeatedly crystallizing is 20%-70%.

18. The preparation method of dihydroquercetin according to claim 15, wherein a material-liquid ratio of the concentrated crude product to the solvent used for the repeated crystallization is 1:3-10.

19. The preparation method of dihydroquercetin according to claim 15, wherein a material-liquid ratio of the primary crystallization substance to the solvent used for the repeated crystallization is 1:5-10.

20. The preparation method of dihydroquercetin according to claim 1, wherein the filter cake is recycled after being washed and purified with hot water.

\* \* \* \* \*